United States Patent [19]

Gibboney et al.

[11] 4,180,440
[45] Dec. 25, 1979

[54] VARIABLE ENDPOINT ANALYZER

[75] Inventors: Dennis A. Gibboney, Mt. Pleasant; John T. Schneider, Apollo; Jerry C. Premus, Scottdale, all of Pa.

[73] Assignee: Fisher Scientific Company, Pittsburgh, Pa.

[21] Appl. No.: 905,572

[22] Filed: May 15, 1978

[51] Int. Cl.$^2$ ............................................. G01N 27/46
[52] U.S. Cl. .................................. 204/1 T; 204/195 T; 422/75
[58] Field of Search .............. 204/195 T, 1 M; 422/75

[56] References Cited

U.S. PATENT DOCUMENTS

| | | | |
|---|---|---|---|
| 2,650,256 | 8/1953 | Lingane | 204/195 T |
| 3,157,471 | 11/1964 | Harrison | 23/230 A |
| 3,275,533 | 9/1966 | Boronkay | 204/195 T |
| 3,730,685 | 5/1973 | Prohaska | 204/195 T |
| 3,738,812 | 6/1973 | Berry et al. | 204/195 T |
| 3,769,178 | 10/1973 | Rothermel | 422/76 |
| 3,870,466 | 3/1975 | Rellstab et al. | 204/195 T |
| 4,055,478 | 10/1977 | Wilson | 204/195 T |
| 4,118,300 | 10/1978 | Victor et al. | 204/195 T |

*Primary Examiner*—T. Tung
*Attorney, Agent, or Firm*—Webb, Burden, Robinson & Webb

[57] ABSTRACT

An improved method of potentiometrically titrating a sample to an unknown endpoint or endpoints is disclosed. The method includes delivering a titrant to the sample until an endpoint or endpoints are reached, while continuously monitoring the volume of the titrant delivered to the sample and continuously monitoring the potential of the sample during titration. The improvement in the method is accurately determining the endpoint or endpoints by establishing a substantially constant rate of change in sample potential during titration proximate to the endpoint or endpoints and maintaining the established rate of change in sample potential by adjusting the rate of delivery of the titrant.

19 Claims, 3 Drawing Figures

VARIABLE ENDPOINT ANALYZER

BACKGROUND OF THE INVENTION

1. Field of the Invention

This invention relates to a method of electrochemical analysis and more particularly to a method of determining the unknown endpoint or endpoints in a potentiometric titration process.

2. Description of the Prior Art

Electrochemical analysis techniques involve the use of electrical properties to correlate with a particular chemical composition. One such electrochemical analysis technique is the field of potentiometry which relates to the use of the measured potential of a sample, as a cell, to determine the concentration of various ionic species within a particular sample. Potentiometry has found wide and accepted use in the titration of ionic species by monitoring the potential of the sample during titration. Potentiometric titration thus provides a relatively accurate method of determining endpoints in the characterization of samples containing ionic species. Numerous methods have been used to accomplish potentiometric titrations with the more recent being by fully automated methods providing an automatic titration.

The application of potentiometric titration must be separated into two distinct areas which present separate problems. The first involves the titration of samples having a known endpoint; the second involves the titration of samples having unknown endpoints.

In any titration the chemical characteristics of the sample must be considered, hence requiring procedural changes. These characteristics include the mutual reactivities of the titrant and the compounds within the sample, and the non-ionic or non-titratable constituent of the sample which affect the chemical interactions of the titrant and reactive compounds. The individual sample characteristics in all instances require the procedural changes which classically have been adjusted based on the experience of those analytical chemists skilled in potentiometric titrations.

For example, in the titration of samples having a known endpoint, the beginning of the titration involves the rapid addition of titrant to the sample, and upon approaching the endpoint, the titrant flow is reduced to allow the sample and titrant to react, thus taking into account any lag in equilibrium of the titrant-sample reaction.

In the potentiometric titration of samples having unknown endpoints several approaches have been used. A series of samples may be titrated to establish the desired titration rate to obtain an accurate endpoint, and once the desired rate is obtained, the final sample is used to determine the endpoint. Another method is a titration which is conducted at a very slow constant rate so that chemical equilibrium can be established with concomitant accuracy in endpoint determination.

In a conventional known endpoint potentiometric process, the titrant delivery rate, through an automatically driven burette, is controlled through a pre-programmed electrical circuit, such as is shown in U.S. Pat. No. 3,157,471, which reduces the rate of titrant delivery as the endpoint is approached. However, the endpoint is a known one with the only variable being the amount of titrant needed to reach this endpoint.

In a typical potentiometric titration the automatically driven burette delivers titrant to the sample. The potential E of the sample is graphically represented on a recorder which plots the potential as ordinate with the total volume added V, as abscissa. The plot resembles an "S" curve with the points of maximum curve inflection indicating the endpoint generally. To obtain the actual endpoint, the midpoint between the inflection points is determined which is also where $dE/dt$ is maximum. In order to more accurately determine the endpoint, the first derivative of the potential with respect to the time, $dE/dt$, is plotted, or otherwise recorded, with respect to volume which gives a sharp peak at the endpoint. In this instance the rate of titrant, $dV/dt$, is held constant in the vicinity of the endpoint. Exemplary of such a method is U.S. Pat. No. 3,769,178.

In the automatic titration of samples having an unknown endpoint, it has been the practice to measure the potential E or its first derivative $dE/dt$ to determine the equivalence which is indicative of an endpoint or endpoints. Measurement of $dE/dt$ requires that the rate of titrant delivery be constant.

This method for unknown endpoint determination may not be satisfactory since the rate of delivery may be too fast to allow accurate readings due to an incapability of the titrant and sample to reach chemical equilibrium in the prescribed time, or may be too slow requiring the time of titration to be too long for efficient analysis.

As can be gleaned from these techniques, the endpoint determination is procedure dependent, rather than chemically dependent on the reaction of the titrant and the sample to achieve an accurate endpoint.

From the foregoing description, the values correlated to obtain an endpoint in the potentiometric titration process are the potential of the cell E and the volume of the titrant to endpoint V. Measuring variations of these values with respect to time and each other are valuable considerations in obtaining precise endpoints. However, as has been demonstrated, when $dV/dt$ is a predetermined and regulated value, the titration process is somewhat inaccurate or slow when titrating for unknown endpoints.

Thus, in accordance with the present invention, a method of potentiometric titration is provided which is dependent upon the chemistry of the particular sample and titrant.

Further, in accordance with the present invention, an automatic titrator is provided which is adapted to determine endpoints upon the chemistry of the particular sample and titrant.

Further, in accordance with the present invention, the method of titration allows for rapid and accurate endpoint determination.

SUMMARY OF THE INVENTION

An improved method of potentiometrically titrating a sample to an unknown endpoint is provided. The method includes delivering a titrant to the sample until an endpoint or endpoints are reached while continuously monitoring the volume of the titrant delivered to the sample and continuously monitoring the potential of the sample during titration. The improvement in the method is accurately determining the endpoint or endpoints by establishing a substantially constant rate of change in sample potential by adjusting the delivery rate of titrant.

An automatic titrator for determining an unknown endpoint or endpoints is also provided which is comprised of: means for establishing a maximum rate of change in sample potential during titration to provide a constant rate of change in sample potential during the titration proximate said endpoint or endpoints; means for generating a first signal proportional to the rate of change in sample potential during titration; means for comparing said first signal to said established maximum rate of change in sample potential; means for signaling the titrant delivery rate control to adjust the titrant delivery rate to prevent exceeding said maximum rate of change in sample potential; means for generating a second signal proportional to said titrant delivery rate; means for generating a third signal proportional to the quotient of the change in potential divided by the titrant delivery rate; and means for generating a fourth signal proportional to the total volume delivered during titration.

The following drawings will further illustrate the principle and operation of the invention.

DETAILED DESCRIPTION OF THE DRAWINGS

Figure 1:
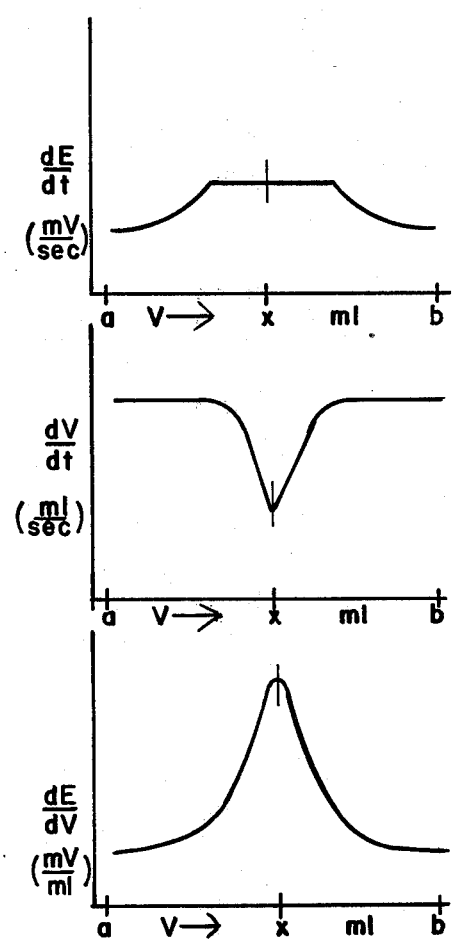
FIG. 1 is a graphic representation of titration curves with dE/dt controlled at a fixed maximum.

In FIG. 1 the relationship of the potential (E), the volume (V) and the time (t) are interdependently rate related and plotted against volume added in a typical potentiometric single endpoint titration to obtain an endpoint volume in accordance with the invention.

In FIG. 1 the endpoint volume x along the abscissa is shown in relation to the time functions dE/dt and dV/dt. dE/dV is used as the endpoint determining function since it is not time dependent, but dependent only upon the chemistry of the particular system.

In performing a typical titration an operator selected maximum dE/dt is adopted for the general chemistry of the particular titrant-sample system involved. At the beginning of the titration, shown as point a, a high rate of titrant addition, usually at maximum burette dispensing rate, may be used without reaching the maximum dE/dt since small changes in potential are effected by large volumes of titrant before the endpoint is approached. Upon approaching the endpoint, E changes relatively fast with small titrant additions, and the maximum dE/dt is reached and held constant by a reduction in dV/dt, preferably, dE/dt is maximized in the range of 0.5 to 50 mv/sec, and more preferably, 0.5 to 10 mv/sec. Thus, with dV/dt set responsive to the constant dE/dt, dV/dt is regulated in accordance with the chemical equilibrium of the system. In order to avoid any relationship of the endpoint determination to procedure, the governing endpoint relationship is dE/dV which is not time, hence not procedurally dependent, thus taking advantage of the relationship:

$$\frac{dE}{dV} = \frac{\frac{dE}{dt}}{\frac{dV}{dt}}.$$

After the endpoint is reached the titration is rapidly completed by increasing dV/dt to maximum burette capacity, a condition converse to the beginning of the titration.

Figure 2:
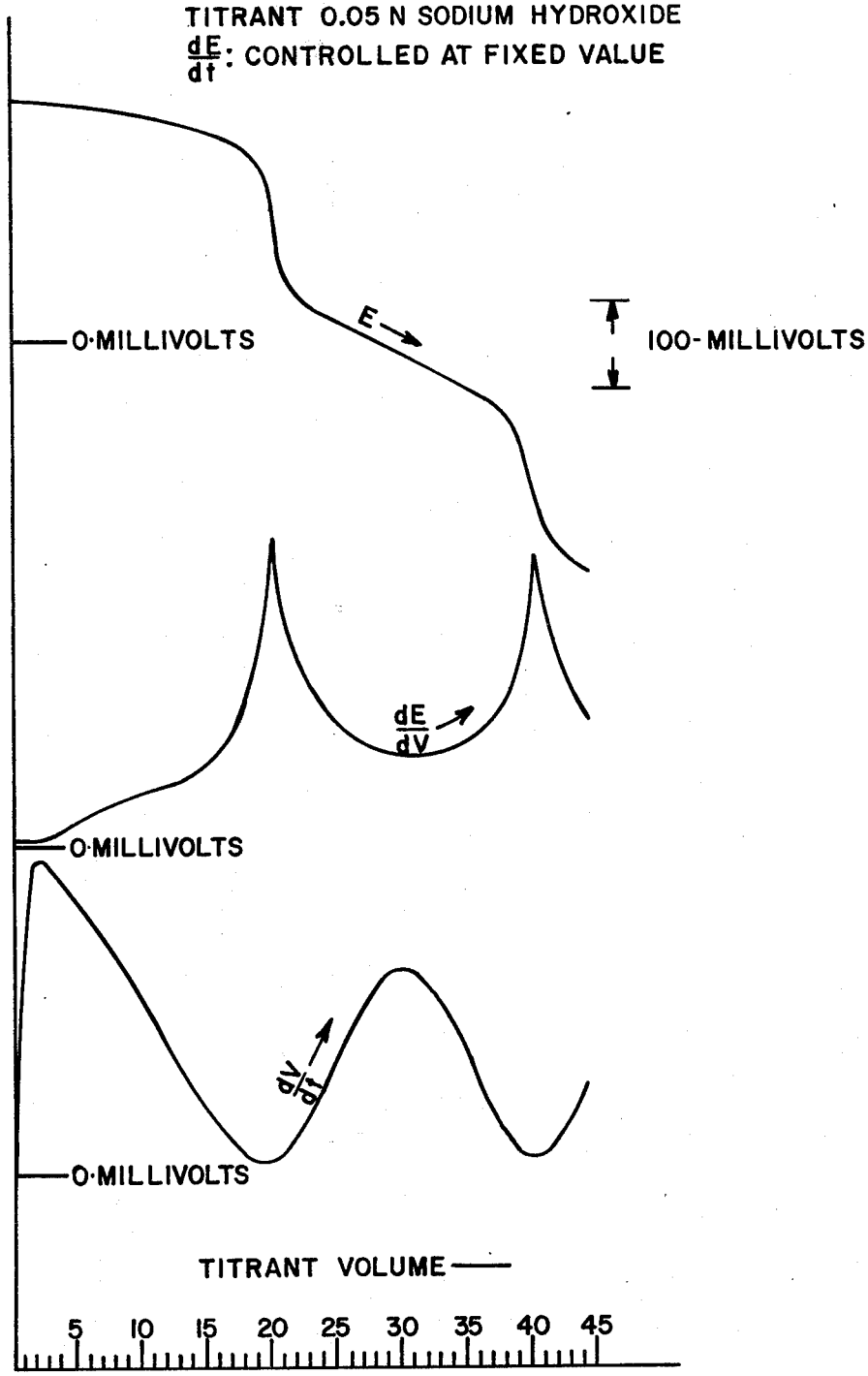
FIG. 2 is a graphic comparison of titration curves monitoring different comparative rates with respect to volume of titrant delivered.

Referring now to FIG. 2, a double endpoint titration is graphically illustrated using 10 mls of a 0.1 N aqueous phosphoric acid solution and a 0.05 N aqueous sodium hydroxide solution as the titrant. The dE/dt is controlled at a maximum fixed value. In FIG. 2, E, dE/dV and dV/dt are plotted in terms of voltage versus total volume with dE/dV being the output for endpoint determination. The peaks along the dE/dV curve represent the total volume of titrant along the abscissa required to reach equivalence points. Thus, 20 mls of 0.05 N, NaOH is required to neutralize the first hydrogen of 10 mls of 0.01 N, $H_3PO_4$ solution and since $$ml \times N = ml \times N$$
$$20 \text{ ml} \times \frac{0.05 \text{ eq}}{ml} = 10 \text{ ml} \times \frac{0.01 \text{ eq}}{ml}$$
$$0.1 \text{ eq NaOH} = 0.1 \text{ eq } H_3PO_4$$

Figure 3:
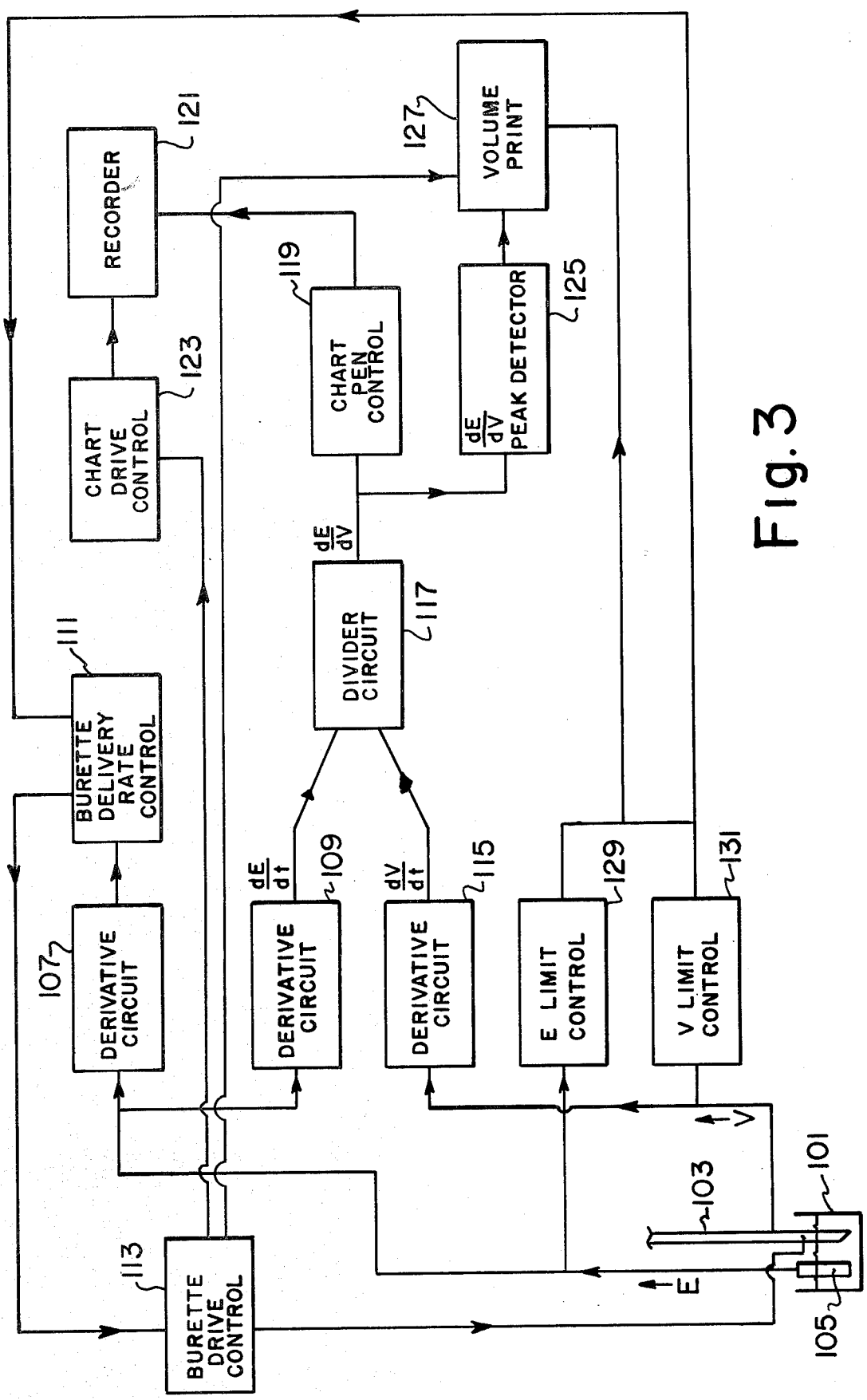
FIG. 3 shows the circuitry of an apparatus used in the practice of the invention.

Referring now to FIG. 3, a preferred apparatus is shown for accomplishing the method of the invention. A sample 101 having an unknown endpoint is supported on a magnetic stirrer (not shown) to obtain constant agitation for an accurate reading of sample potential during titration. A burette 103 containing a titrant is partially immersed in the sample 101 along with an electrode 105 which responds to the potential of the sample 101 during titration. The potential signal from the electrode is directed to two parallel derivative circuits 107 and 109 which generate a continuous signal for dE/dt. The potential signal may be passed through a filter (not shown) to generate a noise free continuous signal for E. The dE/dt signal from circuit 107 is directed to the burette delivery rate control 111 (preferably a voltage control oscillator) which compares the de/dt generated by circuit 107 with an operator predetermined dE/dt. The rate control 111 then signals the burette drive control 113 adjusting the titrant volume delivery rate from burette 103 to obtain a pre-determined maximum dE/dt.

The volume delivery to the sample 101 is signaled to derivative circuit 115 which generates dV/dt. The volume delivery signal may be passed through a filter (not shown) to generate a noise free continuous signal. Further, the volume reading should be pulsed as rapidly as possible to read continuously to obtain an accurate dV/dt. The dV/dt signal from circuit 115 and the dE/dt signal from circuit 109 are divided in divider circuit 117 which generates a signal for dE/dV. The dE/dV signal is directed to the chart pen control 119 of a recorder 121, with chart pen control 119 generating a graphic representation of dE/dV versus V. The chart drive control 123 of recorder 121 is controlled by burette drive control 113 to synchronize the total volume of titrant delivered with the total volume of titrant graphed by recorder 121. An example of the graph generated is shown in the middle graph of FIG. 2. The signal dE/dV is also directed to peak detector 125 which determines the maximum dE/dV in a given titration and signals volume printer 127 which prints the volume of titrant used at the point of maximum dE/dV, thus providing the endpoint volume. The dE/dV peak detector 125 is typically a derivative circuit signaling volume at $d^2E/d^2V$ changing from plus to minus.

The system also includes, as a practical matter, operator set limit controls 129 and 131 to limit the maximum change in potential and the maximum titrant volume respectively, in a given titration.

Thus, when the operator set E and/or V limits have been reached the appropriate limit controls signal the burette delivery rate control 111 and the volume printer 127 stopping the titration and printing the volume of titrant at maximum dE/dV.

Other circuits than that shown may be used to provide the method of the invention to determine the endpoint or endpoints in the titration of unknown samples.

We claim:

1. In the method of potentiometrically titrating a sample to an unknown endpoint or endpoints including: delivering a titrant to the sample until an endpoint or endpoints are reached; continuously monitoring the volume of the titrant delivered to the sample; and continuously monitoring the potential of the sample during titration, the improvement comprising accurately determining said endpoint or endpoints by the steps of:
   (a) generating a first signal proportional to the rate of change with respect to time in sample potential during titration;
   (b) generating a second signal proportional to the titrant delivery rate with respect to time during titration;
   (c) dividing said first signal by said second signal to produce a third signal proportional to the change in potential with respect to the change in volume; and
   (d) monitoring said third signal to identify a signal corresponding to said endpoint or endpoints.

2. The improvement as set forth in claim 1 and including the step of recording at least the signal corresponding to said endpoint or endpoints.

3. The improvement as set forth in claim 1 and including the step of establishing a maximum rate of change in sample potential during titration.

4. The improvement as set forth in claim 1 and including the steps of:
   (e) establishing a substantially constant rate of change in sample potential during titration proximate to the endpoint or endpoints; and
   (f) adjusting the titrant delivery rate to maintain the established rate of change in sample potential.

5. The improvement as set forth in claim 1 and including the steps of:
   (e) establishing a maximum rate of change in sample potential during titration to provide a constant rate of change in sample potential during the titration proximate said endpoint or endpoints; and
   (f) adjusting the titrant delivery rate responsive to said first signal to prevent exceeding said maximum rate of change in sample potential and to maintain said established rate of change in sample potential.

6. The improvement as set forth in claim 5 and including the step of recording at least the signal corresponding to said endpoint or endpoints.

7. The improvement as set forth in claim 5 and including the steps of:
   (g) generating a fourth signal proportional to the total volume delivered during titration; and
   (h) recording said third signal as ordinate and said fourth signal as abscissa during titration.

8. The improvement as set forth in claim 5 and including the steps of:
   (g) generating a fourth signal proportional to the total volume delivered during titration;
   (h) converting said fourth signal to units of volume; and
   (i) printing said total volume delivered when said third signal reaches a maximum.

9. In an automatic titrator for determining the unknown endpoint or endpoints of a sample including means for delivering a titrant to the sample until an endpoint or endpoints are reached; means for continuously monitoring the volume of the titrant delivered to the sample during titration; the improvement comprising:
   (a) means for generating a first signal proportional to the rate of change with respect to time in sample potential during titration;
   (b) means for generating a second signal proportional to the titrant delivery rate with respect to time during titration;
   (c) means for dividing said first signal by said second signal to produce a third signal proportional to the change in potential with respect to the change in volume; and
   (d) means for monitoring said third signal to obtain a signal corresponding to said endpoint or endpoints.

10. The improvement as set forth in claim 9 and including means for recording at least the signal corresponding to said endpoint or endpoints.

11. The improvement as set forth in claim 9 and including means for establishing a maximum rate of change in sample potential during titration.

12. The improvement as set forth in claim 9 and including:
    (e) means for establishing a substantially constant rate of change in sample potential during titration proximate to the endpoint or endpoints; and
    (f) means for adjusting the titrant delivery rate to maintain the established rate of change in sample potential.

13. The improvement as set forth in claim 9 and including:
    (e) means for establishing a maximum rate of change in sample potential during titration to provide a constant rate of change in sample potential during the titration proximate said endpoint or endpoints; and
    (f) means for adjusting the titrant delivery rate to prevent exceeding said maximum rate of change in sample potential and to maintain said established rate of change in sample potential.

14. The improvement as set forth in claim 13 and including means for recording at least the signal corresponding to said endpoint or endpoints.

15. The improvement as set forth in claim 13 and including:
    (g) means for generating a fourth signal proportional to the total volume delivered during titration; and
    (h) means for recording said third signal as ordinate and said fourth signal as abscissa during the titration.

16. The improvement of claim 15 wherein said means for recording said third signal as ordinate and said fourth signal as abscissa is a strip chart recorder.

17. The improvement as set forth in claim 13 and including:
    (i) means for generating a fourth signal proportional to the total volume of titrant delivered during titration;

(j) means for converting said fourth signal to units of volume; and (k) means for printing said total volume delivered when said third signal reaches maximum.

18. The improvement as set forth in claim 13 wherein said first and second signals are generated by derivative circuits.

19. The improvement as set forth in claim 13 wherein said means for generating said third signal is a divider circuit.

* * * * *